United States Patent
Zou et al.

(10) Patent No.: US 9,944,953 B2
(45) Date of Patent: Apr. 17, 2018

(54) METHOD OF EXPRESSING GOLDFISH GFTP1 TRANPOSASE PROTEIN

(71) Applicant: Shanghai Ocean University, Shanghai (CN)

(72) Inventors: Shuming Zou, Shanghai (CN); Xiayun Jiang, Shanghai (CN); Haili Xu, Shanghai (CN); Fei Hou, Shanghai (CN); Luodan Cheng, Shanghai (CN); Xiaodan Shen, Shanghai (CN); Shouchang Deng, Shanghai (CN)

(73) Assignee: Shanghai Ocean University, Shanghai (CN)

( * ) Notice: Subject to any disclaimer, the term of this patent is extended or adjusted under 35 U.S.C. 154(b) by 104 days.

(21) Appl. No.: 15/025,998

(22) PCT Filed: Jan. 4, 2015

(86) PCT No.: PCT/CN2015/070017
§ 371 (c)(1),
(2) Date: Mar. 30, 2016

(87) PCT Pub. No.: WO2015/143930
PCT Pub. Date: Oct. 1, 2015

(65) Prior Publication Data
US 2016/0215299 A1    Jul. 28, 2016

(30) Foreign Application Priority Data

Mar. 24, 2014 (CN) .......................... 2014 1 0108974

(51) Int. Cl.
| | |
|---|---|
| *C12N 9/12* | (2006.01) |
| *C12N 1/21* | (2006.01) |
| *C12N 15/85* | (2006.01) |
| *C12N 15/70* | (2006.01) |
| *C12N 15/89* | (2006.01) |
| *C12N 1/20* | (2006.01) |
| *C12N 9/10* | (2006.01) |

(52) U.S. Cl.
CPC .............. *C12N 15/89* (2013.01); *C12N 1/20* (2013.01); *C12N 9/1096* (2013.01); *C12N 9/1241* (2013.01); *C12N 15/8509* (2013.01); *A01K 2227/40* (2013.01); *C12N 2800/90* (2013.01); *C12Y 207/07* (2013.01)

(58) Field of Classification Search
CPC ........ C12N 15/89; C12N 1/20; C12N 9/1096; C12N 9/1241; C12N 15/8509; C12N 2800/90; A01L 2227/40; C12Y 207/07
See application file for complete search history.

(56) References Cited

U.S. PATENT DOCUMENTS 7,034,115 B1    4/2006  Kawakami

FOREIGN PATENT DOCUMENTS

| CN | 101962659 A | 2/2011 |
|---|---|---|
| CN | 101962660 A | 2/2011 |
| CN | 103981204 A | 8/2014 |
| WO | 0140477 A1 | 6/2001 |

OTHER PUBLICATIONS

Apr. 22, 2015—International Search Report and Written Opinion—PCT App PCT/CN2015/070017.
Jul. 31, 2012—"Goldfish transposase Tgf2 presumably from recent horizontal transfer is active"—Jiang, Xiayun et al.—The Faseb Journal.
Nov. 5, 2014—"Prokaryotic Expression and Purification of Soluble Goldfish Tgf2 Transposase with Transposition Activity"—Xu, Haili et al.—Mol Biotechnol.
Aug. 14, 2007—"Recombinant Tol2 transposase with activity in Xenopus embryos"—Shibano, Takashi, et al.—Federation of European Biochemical Societies.
2001—Molecular Cloning: A Laboratory Manual—Sambrook and Russell—Cold Spring Harbor Press.
Cheng, LD et al., "The goldfish hAT-family transposon Tgf2 is capable of autonomous excision in zebrafish embryos", Nov. 30, 2013, Gene.

*Primary Examiner* — Thaian N Ton
(74) *Attorney, Agent, or Firm* — Banner & Witcoff, Ltd.

(57) ABSTRACT

An expression method of active goldfish gfTP1 transposase protein comprises: constructing an expression vector comprising a gfTP1 transposase reading frame of a goldfish Tgf2 transposon, after transferred into *escherichia coli Rosetta* 1 (DE3), culturing an expression strain until absorbance of a bacteria solution under $OD_{600}$ reaches 0.3-0.4, adding IPTG, culturing under 21-22° C. in shaking of 150-200 rpm, inducing to express soluble recombinant protein, and purifying to obtain a functionally active transposase. Also provided are an expression plasmid and the expression strain of the goldfish gfTP1 transposase protein, and a use of the strain in transgenosis.

6 Claims, 6 Drawing Sheets

Fig. 9 pTgf2-zfβ-actin-eGFP: ATCCGTAGTGCTTGTTACcagaggtg---Tgf2---cacctctgCTTGTTACTGCGCAGTGC
Sample 1: AAGTCGTTTGCATGTACTcagaggtg---Tgf2---cacctctgCATGTACTTGACCGGGAA
Sample 2: ATTCCGTCAGAGATAGATcagaggtg---Tgf2---cacctctgAGATAGATATGCGAACCG
Sample 3: TACATGCTTTTAAGTGCTcagaggtg---Tgf2---cacctctgTAAGTGCTTTGCAAACCA
GTGATGAATAGACATATGcagaggtg---Tgf2---cacctctgGACATATGTCATTGCTCC
Sample 4: ATGTTGTCTATCGATAGTcagaggtg---Tgf2---cacctctgTCGATAGTACATATCCTA

Fig. 10

SEQUENCE LISTING

<160> NUMBER OF SEQ ID NOS: 8

<210> SEQ ID NO 1
<211> LENGTH: 28
<212> TYPE: DNA
<213> ORGANISM: Artificial sequence
<220> FEATURE:
<223> OTHER INFORMATION: PCR Primer

<400> SEQUENCE: 1
cgcggatcca tgttcattgg tcctttgg                                          28

<210> SEQ ID NO 2
<211> LENGTH: 30
<212> TYPE: DNA
<213> ORGANISM: Artificial sequence
<220> FEATURE:
<223> OTHER INFORMATION: PCR Primer

<400> SEQUENCE: 2
ccgctcgagc tactcaaagt tgtaaaacct                                        30

<210> SEQ ID NO 3
<211> LENGTH: 50
<212> TYPE: DNA
<213> ORGANISM: Artificial sequence
<220> FEATURE:
<223> OTHER INFORMATION: Probe

<400> SEQUENCE: 3
cagaggtgta aaagtactta agtaattta cttgattact gtacttaagt                   50

<210> SEQ ID NO 4
<211> LENGTH: 50
<212> TYPE: DNA
<213> ORGANISM: Artificial sequence
<220> FEATURE:
<223> OTHER INFORMATION: Probe

<400> SEQUENCE: 4
cagaggtgta aaagtactaa aaatatttac taaagtgaaa gtacaagtat                  50

<210> SEQ ID NO 5
<211> LENGTH: 2058
<212> TYPE: DNA
<213> ORGANISM: Carassius auratus Ryukin

<400> SEQUENCE: 5
atgtttattg gcccgctgga agtgaccagc tgccatattt attatcataa cgcgcagcat       60
ctggatctgg aaattcgtga aattattacc gtgaaccagt ggaaaaaaat ggaagaagtg      120
tgcgatagca gcgcggcggc gagcagcacc gtgcagaacc agccgcagga tcaggaacat      180
ccgtggccgt atctgcgtga atttttagc tttagcggcg tgaacaaaga tagctttaaa       240
atgaaatgcg tgctgtgcct gccgctgaac aaagaaatta gcgcgtttaa aagcagcccg      300
agcaacctgc gtaaacatat tgaacgtatg catccgaact atctgaaaaa ctatagcaaa      360
ctgaccgcgc agaaacgtaa aattggcacc agcacccatg cgagcagcag caaacagctg      420
aaagtggata gcgtgtttcc ggtgaaacat gtgagcccgg tgaccgtgaa caaagcgatt      480
ctgcgttata ttattcaggg cctgcatccg tttagcaccg tggatctgcc gagctttaaa      540
gaactgatta gcgcgctgca gccgggcatt agcgtgatta cccgtccgac cctgcgtagc      600
aaaattgcgg aagcggcgct gattatgaaa cagaaagtga ccgcggcgat gagcgaagtg      660

```
gaatggattg cgaccaccac cgattgctgg accgcgcgtc gtaaaagctt tattggcgtg      720
accgcgcatt ggattaaccc gggcagcctg aacgtcata gcgcgtttgc gctggcgtgc      780
aaacgtctga tgggcagcca tacctttgaa gtgctggcga gcgcgatgaa cgatattcat     840
agcgaatatg aaattcgtga taaagtggtg tgcaccacca ccgatagcgg cagcaacttt    900
ctgaaagcgt ttcgtgtgtt tggcgtggaa acaacgata ttgaaccca ggcgcgtcgt      960 tgcgaaagcg atgataccga tagcgaaggc tgcggcgaag cagcgatgg cgtggaatgc     1020 caggatgcga ccgtgtgct ggatcaggat gatggctttg aatttcagct gccgaaacat     1080
cagaaatgcg cgtgccatct gctgaacctg gtgagcagcg tggatgcgca aaagcgctg     1140 agcaacgaac attataaaaa actgtatcgt agcgtgtttg caaatgcca ggcgctgtgg     1200 aacaaaagca gccgtagcgc gctggcggcg aagcggtgg aaagcgaaag ccgtctgcag     1260
ctgctgcgtc cgaaccagac ccgttggaac agcacctta tggcggtgga tcgtattctg     1320
cagatttgca agaagcggg cgaaggcgcg ctgcgtaaca tttgcaccag cctggaagtg     1380
ccgatgttta acccggcgga aatgctgttt ctgaccgaat gggcgaacac catgcgtccg    1440
gtggcgaaag tgctggatat tctgcaggcg aaaccaaca cccagctggg ctggctgctg     1500
ccgagcgtgc atcagctgag cctgaaactg cagcgtctgc atcatagcct gcgttattgc    1560
gatccgctgg tggatgcgct gcagcagggc attcagaccc gttttaaaca tatgtttgaa    1620
gatccggaaa ttattgcggc ggcgattctg ctgccgaaat tcgtaccag ctggaccaac     1680 gatgaaacca ttattaaacg tggcatggat tatattcgtg tgcatctgga accgctggat    1740
cataaaaaag aactggcgaa cagcagcagc gatgatgaag attttttttgc gagcctgaaa   1800 ccgaccaccc atgaagcggg caaagaactg gatggctatc tggcgtgcgt gagcgatacc    1860
cgtgaaagcc tgctgacctt tccggcgatg tgcagcctga gcattaaaac caacaccccg    1920
ctgccggcga gcgcggcgtg cgaacgtctg tttagcaccg cgggcctgct gtttagcccg    1980
aaacgtgcgc gtctggatac caacaacttt gaaaaccagc tgctgctgaa actgaacctg   2040 cgttttttata actttgaa                                                 2058

<210> SEQ ID NO 6
<211> LENGTH: 16
<212> TYPE: PRT
<213> ORGANISM: Carassius auratus Ryukin

<400> SEQUENCE: 6

Gly Ser Ser His His His His His His Ser Ser Gly Leu Val Pro Arg
1               5                   10                  15

<210> SEQ ID NO 7
<211> LENGTH: 14
<212> TYPE: PRT
<213> ORGANISM: Carassius auratus Ryukin

<400> SEQUENCE: 7

Val Phe Gly Val Glu Asn Asn Asp Ile Glu Thr Glu Ala Arg
1               5                   10
```

```
<210> SEQ ID NO 8
<211> LENGTH: 14
<212> TYPE: PRT
<213> ORGANISM: Carassius auratus Ryukin

<400> SEQUENCE: 8

Val Leu Asp Gln Asp Asp Gly Phe Glu Phe Gln Leu Pro Lys
1               5                   10
```

METHOD OF EXPRESSING GOLDFISH GFTP1 TRANPOSASE PROTEIN

TECHNICAL FIELD OF THE INVENTION

The present invention refers to the field of biotechnology, particularly to a method of expressing active recombinant goldfish Tgf2 transposase protein, and the insertion efficiency mediated by the protein in zebrafish and blunt snout bream.

BACKGROUND OF THE INVENTION

DNA transposons are mobile genetic elements that can change positions within the genome(s) utilizing a "cut-and-paste" mechanism, and have an important value in the genetic modification of biological genome. Two essential sequence elements participate in transposition: (1) flanked inverted terminal repeats (ITRs) involved in specific recognition and (2) active transposases. An autonomous DNA transposon could usually transcribe and translate active transposase to catalyze the transposition of the transposon. However, the coding regions for transposase in most of the vertebrate DNA transposons mutated and lost their activity during the evolutionary process because of the vertical inactivation in hosts. Even so, the coding regions for transposase can be reconstructed according to conserved sequence for transposase in inactivated transposon by bioinformatics, such as the artificially constructed Sleeping Beauty transposition system and Frog Prince transposition system that could mediate transposition in animal embryos or cells.

Several autonomous transposons have been successively discovered in fish in the last decade. For example, Tol2 transposon, which is identified in medaka and belongs to hAT (hobo-Ac-Tam3) transposon superfamily, is the first natural active transposon found in vertebrates. The transcribed mRNA in vitro of Tol2 transposase can mediate efficient insertion of transposable elements, and can achieve efficient transposition in the cells of vertebrates including zebrafish, clawed frog, chicken and mammals. Goldfish Tgf2 transposon belonging to hAT transposon superfamily is also a natural active transposon. The Tgf2 transposon system can efficiently transpose in the embryos of goldfish, zebrafish and the other Cyprinoid fishes (Reference 1: X. Y. Jiang, X. D. Du, Y. M. Tian, R. J. Shen, C. F. Sun, S. M. Zou, Goldfish transposase Tgf2 presumably from recent horizontal transfer is active, FASEB J. 26 (2012) 2743-2752. Reference 2: L. D. Cheng, X. Y. Jiang, Y. M. Tian, J. Chen, S. M. Zou, The goldfish hAT-family transposon Tgf2 is capable of autonomous excision in zebrafish embryos, Gene (2013) http://dx.doi.org/10.1016/j.gene.2013.11.084.). Additionally, a Tc1-like transposon from flatfish (*Pleuronectes platessa*), Passport, also has transposition activity in the vertebrate cells.

Recently, the common method is that the donor plasmid containing the left and right ends of the transposon and transposase mRNA are coinjected into fertilized fish eggs at the 1-2 cell stage. The transposase mRNA is firstly translated to transposase protein after injection into fertilized eggs, which then mediates the insertion of target gene or element into the fish genome. The transcription of the transposase mRNA needs to be completed in vitro, but the general fish farms do not have the conditions for synthesis and cryopreservation. In addition, the translation of transposase takes some time, and usually produces transgenic chimeras (T. Shibano, M. Takeda, I. Suetake, K. Kawakami, M. Asashima, S. Tajima, M. Taira, Recombinant Tol2 transposase with activity in Xenopus embryos, FEBS Lett. 581 (2007) 4333-4336.). However, the occurrence of chimeras can be effectively prevented by the direct injection of active transposase protein.

The reference 1 (X. Y. Jiang, X. D. Du, Y. M. Tian, R. J. Shen, C. F. Sun, S. M. Zou, Goldfish transposase Tgf2 presumably from recent horizontal transfer is active, FASEB J. 26 (2012) 2743-2752.) reported that an active Tgf2 transposon of hAT transposon superfamily was found in goldfish, and it had 7 kinds of mRNA transcripts, which encoded putative transposases of 3 different lengths of 686 (gfTP1), 650 (gfTP2-3), and 577 (gfTP4-7) aa residues. The active recombinant goldfish Tgf2 transposase protein has not been reported at present.

Recombinant protein is the protein obtained by DNA or RNA recombinant technique. The route can be divided into in vitro and in vivo methods, which are all based on gene recombination technology that recombinant vector connected gene fragment that can be translated into target protein is constructed, and then transferred to the host cell that can express target protein to express the particular recombinant protein molecule. There are usually some problems in the recombinant protein expression process concluding that the recombinant protein could not be expressed, the expression level is low, the expression product has no or a low activity, etc. Many factors affect the expression level and activity of the recombinant protein, such as the modification of target gene in the gene level, the selection of promoter, the inducer concentration, induction temperature and induction time in the bacterial fermentation, etc. The recombinant protein production is a process requiring theory and practice, and many problems need to be solved in order to obtain an optimal construction, expression and purification scheme.

SUMMARY OF THE INVENTION

The first objective of this invention is to provide a method of expressing goldfish gfTP1 transposase protein in view of the deficiencies in the prior art.

The second objective of this invention is to provide a plasmid of expressing the goldfish gfTP1 transposase protein.

The third objective of this invention is to provide a strain of expressing the goldfish gfTP1 transposase protein.

The fourth objective of this invention is to provide a use of the strain of expressing goldfish gfTP1 transposase protein.

The fifth objective of this invention is to provide a method of transgene.

To achieve the above first objective, the technical scheme taken in this invention is:

A method of expressing goldfish gfTP1 transposase protein, comprising the following steps:
culturing a strain of expressing goldfish gfTP1 transposase protein until the $OD_{600}$ of the culture reach to 0.3-0.4,
adding IPTG,
shaking at 150-200 rpm at 21-22° C.;
said strain of expressing goldfish gfTP1 transposase protein is *E. coli Rosetta* 1 (DE3) transformed with plasmid of expressing goldfish gfTP1 transposase protein;
said plasmid of expressing goldfish gfTP1 transposase protein is constructed by the following method comprising: inserting nucleotide sequence shown in SEQ ID NO. 5 into plasmid pET-28a between BamHI and XhoI sites.

Preferably, the method of expressing goldfish gfTP1 transposase protein comprising the following steps:
culturing a strain of expressing goldfish gfTP1 transposase protein until the $OD_{600}$ of the culture reach to 0.35,
adding IPTG,
shaking at 150-200 rpm at 22° C.
Preferably, the time of shaking is 4-6 h.
Preferably, the concentration of IPTG in culture is 0.6-1.0 mM.

To achieve the above second objective, the technical scheme taken in this invention is:
A plasmid of expressing goldfish gfTP1 transposase protein, characterized in that the plasmid is constructed by the following method comprising:
inserting nucleotide sequence shown in SEQ ID NO. 5 into plasmid pET-28a between BamHI and XhoI sites.

To achieve the above third objective, the technical scheme taken in this invention is:
A strain of expressing goldfish gfTP1 transposase protein, characterized in that the strain is E. coli Rosetta 1 (DE3) transformed with said plasmid of expressing goldfish gfTP1 transposase protein.

To achieve the above fourth objective, the technical scheme taken in this invention is:
A use of the strain of expressing goldfish gfTP1 transposase protein in mediating transgene.

To achieve the above fifth objective, the technical scheme taken in this invention is:
A method of transgene, characterized in that the method comprising:
culturing the strain of expressing goldfish gfTP1 transposase protein,
purifying the goldfish gfTP1 transposase protein,
then co-injecting the goldfish gfTP1 transposase protein into fertilized egg or embryo of vertebrate with donor plasmid for transgene.

In an embodiment of this invention, wherein the donor plasmid for transgene is pTgf2-zfβ-actin-eGFP, the vertebrate is zebrafish or blunt snout bream.

The positive effects of this invention:
The expression plasmid pET-28a-gfTP1 containing gfTP1 transposase-encoding ORF of goldfish Tgf2 transposon was constructed in this invention. Soluble and functional recombinant transposase protein was expressed in prokaryotic strain Rosetta 1 (DE3) E. coli and purified. The induction conditions used in this invention improved the expression level of the recombinant transposase protein significantly, making a surprising technical effect. The expressed recombinant transposase protein was confirmed to mediate transposition well according to transgene experiments in zebrafish and blunt snout bream. This invention provides an efficient method to transgene and gene insertion in genome of fish and other vertebrates.

BRIEF DESCRIPTION OF THE DRAWINGS

FIG. 1 shows the vector map of plasmid pET-28a.

FIG. 3 is SDS-PAGE electrophoretogram of recombinant goldfish gfTP1 transposase produced in different induction conditions. The E. coli strain Rosetta 1 (DE3) carrying pET-28a-gfTP1 recombinant plasmid was cultured at 22° C., and the protein expression was initially induced at early-log phase ($OD_{600}$=0.3-0.4) and mid-log ($OD_{600}$=0.6-0.7) with 0.8 mM IPTG respectively. M1: standard molecular mass marker; Lane 0: lysates of cells not containing plasmids after treatment with 0.8 mM IPTG; Lane 1: lysates of cells carrying the recombinant plasmids without IPTG induction. Lanes 2-4: lysates of cells containing the recombinant plasmids initially induced at early-log phase ($OD_{600}$=0.3-0.4) culture for 4, 6, and 9 h, respectively. Lanes 5-7: lysates of cells containing the recombinant plasmids initially induced at mid-log ($OD_{600}$=0.6-0.7) phase culture for 4, 6, and 9 h, respectively. The arrow instructs the recombinant protein band.

FIG. 4 shows the purification of recombinant goldfish gfTP1 transposase. (a) SDS-PAGE electrophoretogram of the recombinant goldfish gfTP1 transposase. The E. coli strain Rosetta 1 (DE3) carrying the recombinant pET-28a-gfTP1 plasmid grew in LB medium at 22° C., with early log ($OD_{600}$=0.3-0.4) phase culture induced with 0.8 mM IPTG. M1: standard molecular mass marker; Lane 0: lysates of cells carrying the recombinant plasmids without IPTG induction; Lane 1: lysates of cells carrying the recombinant plasmids with IPTG induction; Lane 2: proteins containing fusion tags were collected from bacterial lysates loaded into the $Ni^{2+}$-affinity column eluted by imidazole solutions. (b) map of western blotting. M2: pre-dyed standard molecular marker. Lane 0: lysates of cells containing the recombinant plasmids without IPTG induction. Lane 1: lysates of cells containing the recombinant plasmids with IPTG induction when $OD_{600}$=0.3-0.4.

FIG. 5 shows the identification of recombinant goldfish gfTP1 transposase by MALDI-TOF/TOF tandem mass spectrometry. (a) putative recombinant goldfish gfTP1 transposase sequence expressed by the plasmid pET28a-gfTP1. Trypsin cleavage sites related to peptide fragments are marked by vertical arrows. The amino acids of 1-34 marked by underline are those incorporated by the recombinant plasmid. The dashed lines above sequences denote enzymatic fragments corresponding to MS/MS spectra. After trypsin hydrolysis, recombinant goldfish gfTP1 transposase solution was injected into a mass spectrometer. The different peptides were sorted and subjected to further analysis. (b)-(d) MS/MS spectra of peptide fragments of the recombinant transposase: (b) GSSHHHHHHSSGLVPR, (c) VFGVENNDIETEAR, and (d) VLDQDDGFEFQLPK. The peaks representing b-, and y-type ions are labeled.

FIG. 6 shows EMSA of DNA binding activity of recombinant goldfish gfTP1 transposase. The 50 bp sequences of left and right ends of goldfish Tgf2 transposon labeled by biotin were used as probes. The DNA binding activity was verified by EMSA, using non-denaturing polyacrylamide gel electrophoresis at 80 V for 1.0 h. Lane 1: biotin-labeled probes based on left (or right) end; Lane 2: the supernatant of cells without IPTG induction; Lane 3: co-incubation complex of biotin-labeled cold probes for control and the purified recombinant goldfish gfTP1 transposase; Lane 4: co-incubation complex of biotin-labeled probes based on Tgf2 left (or right) end and the purified 1× recombinant goldfish gfTP1 transposase; Lane 5: co-incubation complex of biotin-labeled probes based on Tgf2 left (or right) end and the purified 10× recombinant goldfish gfTP1 transposase.

FIG. 9A, B are fluorescence images of EGFP expression in blunt snout bream fertilized eggs at 72 h after co-injection of the donor plasmid pTgf2-zfβ-actin-eGFP and recombinant goldfish gfTP1 transpopsase, showing that EGFP was expressed strongly and ubiquitously. C, D: fluorescence images of EGFP expression in blunt snout bream fertilized eggs only injected the donor plasmid pTgf2-zfβ-actin-eGFP at 72 h after injection, showing that EGFP was expressed weakly in part of tissue.

DETAILED DESCRIPTION OF THE PREFERRED EMBODIMENT

The following are the detailed descriptions of embodiments of this invention with reference to the drawings. The methods without specific conditions in the following embodiments are usually done in accordance with normal conditions, such as the said conditions in Molecular Cloning A Laboratory Manual edited by J. Sambrook et al. and published by Science Press (China) in 2002, or the conditions recommended by manufacturer. Percentages and parts are by weight unless otherwise indicated.

Figure 1:
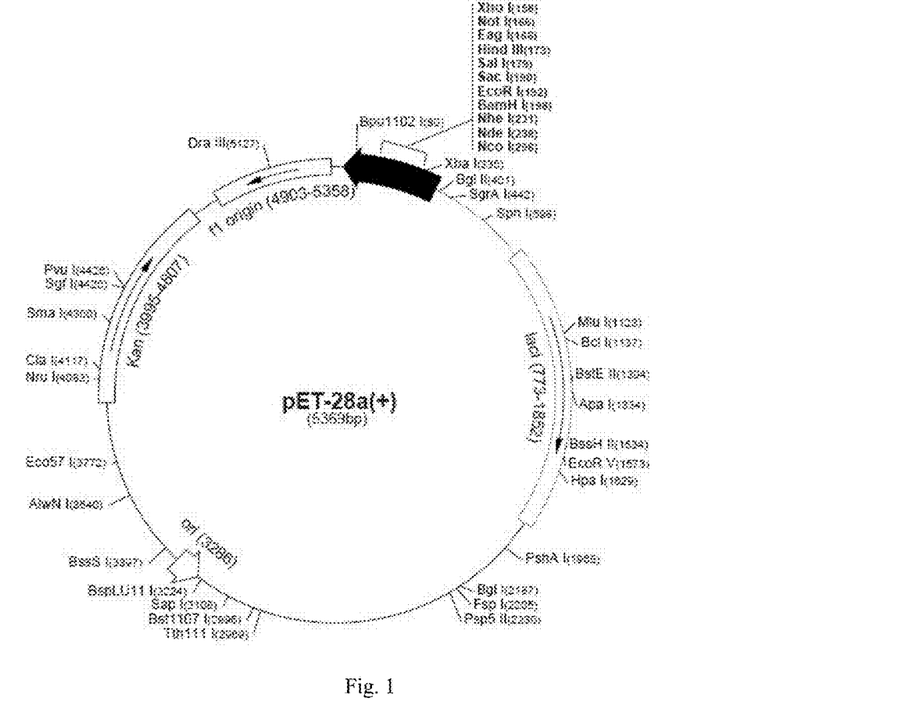

Embodiment 1 Expression and Identification of Recombinant Goldfish gfTP1 Transposase Protein 1. Materials and Methods
1.1. Materials Goldfish embryos were provided by Qingpu Fish Breeding Experimental Station of Shanghai Ocean University. The primers were synthesized by Sangon Biotech (Shanghai) Co., Ltd. $Ni^{2+}$-affinity column was purchased from GE Healthcare. Ultrafiltration tubes were purchased from Millipore Corporation, USA. The restriction enzyme, DNA Polymerase and T4 DNA ligase were purchased from Takara. The vector pET-28a and the host strains DH5α, BL21 (DE3) and Rosetta 1 (DE3) were purchased from Merck. Electrophoretic Mobility Shift Assay (EMSA) Kits were purchased from Beyotime Biotechnology. The other reagents were purchased from Sangon Biotech (Shanghai) Co., Ltd, and were all of analytical grade or higher purity.
1.2. Methods
1.2.1. Molecular Cloning of the gfTP1 Transposase-Encoding ORF Total RNA was isolated from ten Ryukin goldfish (Latin name: Carassius auratus Ryukin) embryos at 24 hours post-fertilization using TRIzol reagent (Invitrogen). Single stranded cDNA was reverse-transcribed from 1 µg total RNA using MMLV reverse transcriptase and oligo-dT primers of TaKaRa RNA PCR Kit (AMV) Ver. 3.0. A pair of primers designed basing on the goldfish Tgf2 transposon ORF (GenBank JN886586) are as follows: the upstream primer, 5'-CGCGGATCCATGTTCATTGGTCCTTTGG-3' (SEQ ID NO. 1), and the downstream primer, 5'-CCG CTCGAGCTACTCAAAGTTGTAAAACCT-3' (SEQ ID NO. 2). The upstream and downstream primer contained BamHI and XhoI restriction enzyme sites (marked by underline) respectively. PCR was performed using the single stranded cDNA as the template, the primers, and Pfu DNA polymerase, with the procedure: 94° C. 5 min, then 94° C. 30 s, 55° C. 30 s, 72° C. 60 s, for 35 cycles, finally extended at 72° C. for 5 min. The amplified products were purified by 1.2% agarose gel electrophoresis running at 5 V/cm in TBE buffer. The target fragments in agarose gel were tapped and recovered and cloned into pMD19-T vector (TaKaRa), transformed into DH5a E. coli cells. The positive clones were picked into LB liquid medium with 506 µg/mL ampicillin and shaken overnight at 37° C. 200 µl bacterial liquid was stored by glycerin, and sent to Sangon Biotech (Shanghai) Co., Ltd to be sequenced from both directions. Then, the constructed plasmid pMD-19T-gfTP1 was obtained.
1.2.2. Construction of Plasmid for Expressing Goldfish gfTP1 Transposase The plasmid pMD-19T-gfTP1 was digested with BamHI and XhoI restriction enzymes, and the digested products were purified by 1.2% agarose gel electrophoresis running at 5 V/cm in TBE buffer. The target fragments were tapped and recovered from the agarose gels to obtain the double digested products gfTP1. The vector pET-28a showed in FIG. 1 was digested with BamHI and XhoI restriction enzymes, and the digested products were purified by 1.2% agarose gel electrophoresis. The target fragments were tapped and recovered from the agarose gels to obtain the double digested products pET-28a. The obtained double digested products pET-28a and gfTP1 were ligated using T4 DNA ligase to generate prokaryotic expression vector pET28a-gfTP1. Then the plasmids pET28a-gfTP1 were respectively transformed into BL21 E. coli competent cells and Rosetta 1 (DE3) E. coli competent cells, and the positive clones were examined by PCR, restriction enzyme digestion and DNA sequencing.
1.2.3. Prokaryotic Expression of Goldfish gfTP1 Transposase 4 ml of an overnight culture of the positive Rosetta 1 (DE3) E. coli bacterial liquid was added to 100 ml of LB medium with the following formula: Tryptone 10 g/L, Yeast extract 5 g/L, NaCl 10 g/L, and shaken at 37° C. When the culture reached a predetermined $OD_{600}$ value (6 gradients: 0.3, 0.35, 0.4, 0.6, 0.65 and 0.7), 0.8 mM IPTG was added to induce protein expression, with additional shaking at 180 rpm at 22° C. for 5 h. The culture was centrifuged at 10,000 g for 10 min at 4° C., re-suspended in phosphate buffer (12 mM phosphate, 125 mM NaCl, pH 8.0) and then frozen at −80° C. The thawed cells were lysed by sonication and centrifuged at 12,000 g for 15 min at 4° C. The lysate, supernatant, and pellet were subjected to SDS-PAGE and then stained by Coomassie brilliant blue referring to the literature: U. K. Laemmli, Cleavage of structural proteins during the assembly of the head of bacteriophage T4, Nature 277 (1970) 680-685. The supernatant was purified using $Ni^{2+}$-affinity column.
1.2.4. Purification of Recombinant Goldfish gfTP1 Transposase The supernatant collected from sonicated lysates was loaded onto a $Ni^{2+}$-affinity column in a FPLC AKTA Purifier system and equilibrated with 10 column volumes of binding buffer. The column was washed with elution buffer (500 mM sodium phosphate, 0.5 M NaCl, 500 mM imidazole, pH 7.4) at a flow rate of 1 ml/min using a linear gradient within 5 column volumes. Protein concentrations were monitored at 280 nm. The elution peak was analyzed by SDS-PAGE and Coomassie brilliant blue staining. The purified recombinant goldfish gfTP1 transposase concentrated by ultrafiltration was stored as a 20% glycerol stock at −80° C.

1.2.5. Western Blotting

The purified recombinant goldfish gfTP1 transposase was electrophoresed on gels and transferred to PVDF membranes at 80 V for 1 h. The membranes were blocked for 1 h at room temperature with 5% non-fat milk and incubated for 2 h with anti-(His)6 monoclonal antibody. After three washes with 60 ml TBST buffer, the membranes were incubated with sheep anti-rabbit IgG-HRP for 1 h, washed by TBST buffer, treated with enhanced chemiluminescence reagents, exposed to X-ray films, and photographed.

1.2.6. Identification of Recombinant Goldfish gfTP1 Transposase

Recombinant goldfish gfTP1 transposase was excised from SDS-PAGE gels and digested with trypsin. Peptide fragments of the transposase were identified using MALDI-TOF/TOF.

1.2.7. DNA Binding Activity Assay of Recombinant Goldfish gfTP1 Transposase

DNA binding activity of the recombinant goldfish gfTP1 transposase was evaluated by DNA binding activity assay (EMSA) using EMSA Biotin Labeling Kit. Tgf2 ITRs and STRs of left and right arm with a length of 50 bp was labeled by biotin. The probes basing on left and right arm were respectively as follows:

```
                                        (SEQ ID NO. 3)
5'-CAGAGGTGTAAAAGTACTTAAGTAATTTTACTTGATTACTG
TACTTAAGT-3', (SEQ ID NO. 4)
5'-CAGAGGTGTAAAAGTACTAAAAATATTTACTAAAGTGAAAG
TACAAGTAT-3'.
```

The DNA probes and recombinant goldfish gfTP1 transposase were incubated at 25° C. for 0.5-1 h. After electrophoresed on 4% PAGE gels at 80 V for 0.5-1.5 h, the proteins on PAGE gels were transferred to nylon membranes at 80 V for 1.5 h. The membranes were irradiated by UV rays with the irradiation intensity of 120 mJ/cm$^2$ for 50 s, incubated using EMSA Kit, treated with enhanced chemiluminescence reagents, exposed to X-ray films, and photographed.

Figure 2:
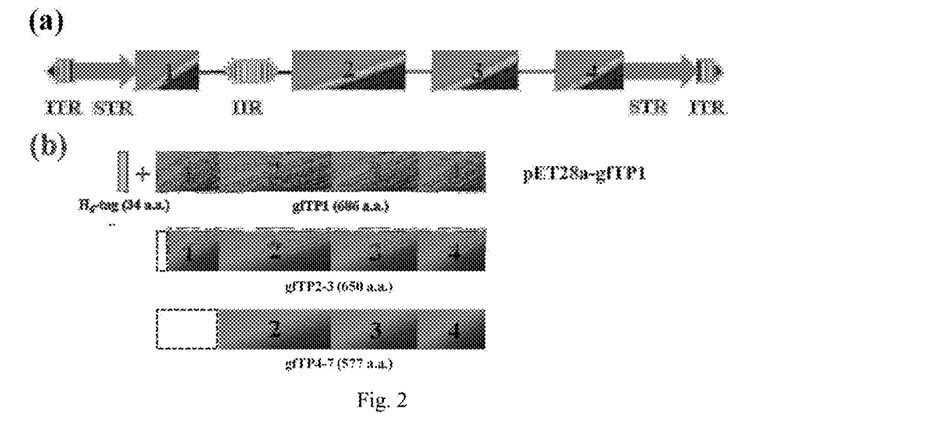
FIG. 2 shows the construction of the pET-28a-gfTP1 vector expressing the recombinant goldfish gfTP1 transposase. (a) structure of Tgf2 transposon (4720 bp full length). ITR: inverted terminal repeat; STR: subterminal inverted repeat; IIR: internal inverted repeat. The black lines correspond to the introns of Tgf2 transposon. The black rectangular boxes correspond to the exons of Tgf2 transposon. (b) structure of the recombinant gfTP1 transposase containing (His)$_6$-tag. The dashed line frames denote the deletion of aa residues.

2. Results and Discussion 2.1. Construction of Expression Vector of Recombinant Goldfish gfTP1 Transposase The goldfish hAT-superfamily transposon Tgf2 is 4,720 bp in full length and consists of four exons (FIG. 2a). Tgf2 transposase has 7 kinds of mRNA transcripts (GenBank JN886586-JN886592), which encode 3 different kinds of transposases gfTP1 (686 aa), gfTP2-3 (650 aa) and gfTP4-7 (577 aa) (FIG. 2b). Among them, the transposase gfTP1 was 109 aa residues longer than the transposase gfTP4-7, while the transposase gfTP2-3 was 73 aa residues longer than the transposase gfTP4-7, and the other aa residues were exactly the same. The cDNA of the transposase gfTP1 expressed in this invention was 2,633 bp in full length, and the 2,058 bp length coding region translating 686 aa residues was the longest transcript encoded by goldfish Tgf2 transposon.

The gfTP1 transposase-encoding ORF sequence showed as SEQ ID NO. 5 was amplified using the total RNA of Ryukin goldfish embryos at 24 hpf as template, and cloned into expression vector pET-28a. The constructed recombinant prokaryotic expression vector pET28a-gfTP1 contained (His)6-tag encoding 34 aa residues (FIG. 2b). The theoretical length of the recombinant goldfish gfTP1 transposase was 720 aa residues, and the molecular weight of the recombinant protein theoretically calculated by ProtParam was 79.4 kDa.

2.2. Expression of Recombinant Goldfish gfTP1 Transposase

The purpose of this invention was to obtain active recombinant goldfish gfTP1 transposase protein, and thus how to express soluble recombinant transposase but not in inclusion bodies was the key factor to succeed. This invention used Rosetta 1 (DE3) E. coli instead of BL21 (DE3) E. coli as host strain to solve the codon bias problem existing in eukaryotic gene expression in E. coli.

The expression of recombinant goldfish gfTP1 transposase did not be detected in any expression condition when the recombinant plasmid was transformed into BL21 (DE3) E. coli cells.

Figure 3:
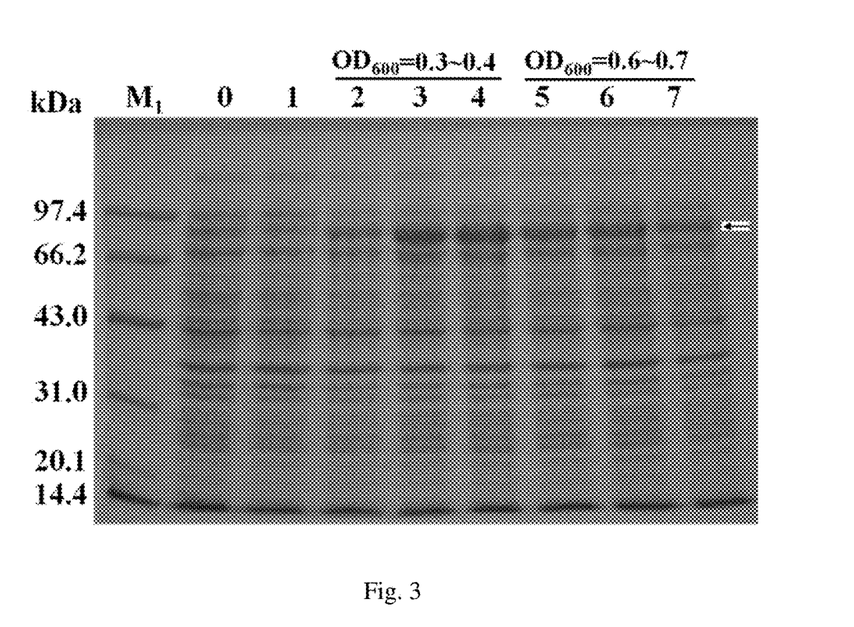

The expression conditions in Rosetta 1 (DE3) E. coli including IPTG concentration, induction temperature and bacterial liquid concentration when IPTG was added were optimized in order to overcome the problem of low levels of foreign protein expressed in prokaryotes. We found that IPTG concentration had little effect on the expression level of the soluble transposase, but the induction temperature had significant effect, with the result that a large amount of recombinant goldfish gfTP1 transposase was induced at 22° C. SDS-PAGE gel electrophoresis showed an obvious protein band of ~80 kDa, in agreement with our estimate about the molecular weight of recombinant goldfish gfTP1 transposase (FIG. 3). However, the expression level of the recombinant protein was significantly affected by the bacterial liquid concentration when IPTG was added in this study, showing that more proteins were produced when IPTG was added at early log phase ($OD_{600}$=0.3-0.4) than at the mid-log phase ($OD_{600}$=0.6-0.7) (FIG. 3). Therefore, a large amount of soluble recombinant goldfish gfTP1 transposase protein could be expressed by Rosetta 1 (DE3) E. coli cells carrying the recombinant plasmid when 0.8 mM IPTG was added at early log phase ($OD_{600}$=0.3-0.4) at 22° C.

2.3. Purification of Recombinant Goldfish gfTP1 Transposase

The cells collected from culture were frozen at −80° C., thawed, sonicated and centrifuged. The collected supernatants were loaded onto a $Ni^{2+}$-affinity column using an AKTA FPLC system, and the elution peak was collected and analyzed by SDS-PAGE, showing that the molecular weight of recombinant goldfish gfTP1 transposase illustrated on the electrophoretogram was in accord with the theoretical estimate. These results suggested that soluble recombinant goldfish gfTP1 transposase were purified, while avoiding co-purification of other proteins (FIG. 4a).

Figure 4:
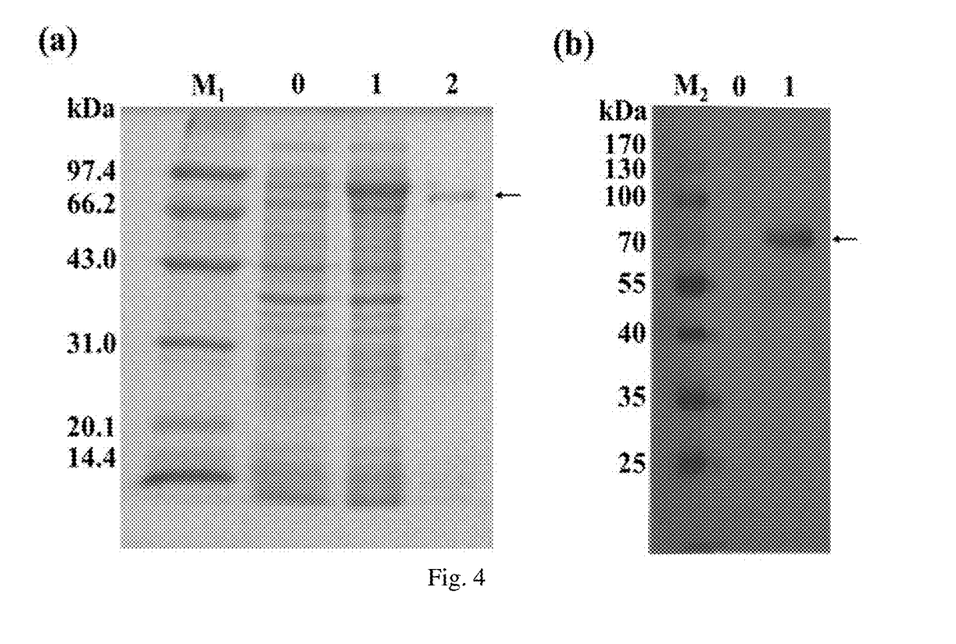

Western blotting assays using antibody specific to the fused (His)6-tag displayed a single band corresponding to recombinant goldfish gfTP1 transposase in the lysates (FIG. 4b).

2.4. Identification of Recombinant Goldfish gfTP1 Transposase

Figure 5:
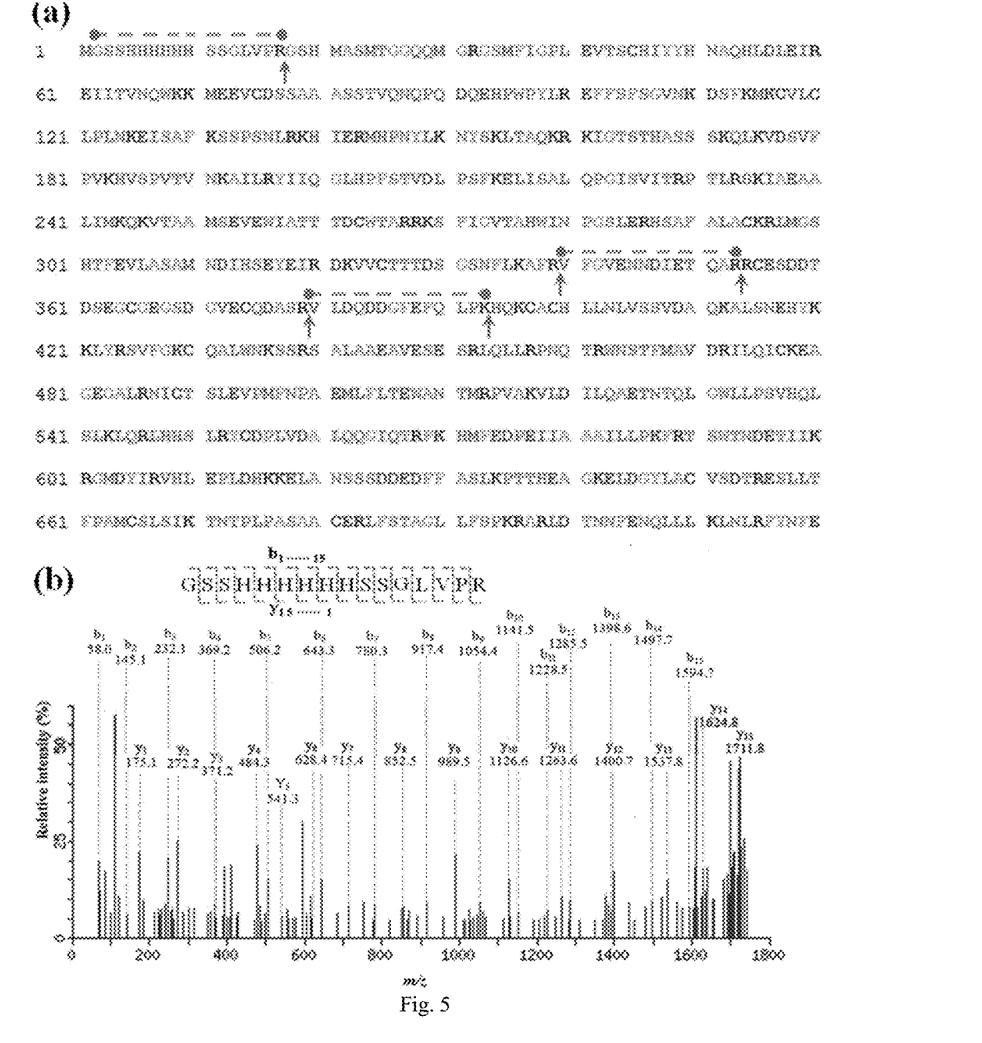

The recombinant proteins were excised from SDS-PAGE gels, digested with trypsin and subjected to MALDI-TOF/TOF tandem MS analysis, and the results confirmed that the chromatographically purified protein was indeed the recombinant goldfish gfTP1 transposase. The MS/MS spectra of three sets of oligopeptide fragments were shown in FIG. 5. The search using Mascot software showed that two of the oligopeptide fragments corresponded to aa residue sequences encoded by ORF of goldfish gfTP1 transposase (FIG. 5a, c, d).

The first oligopeptide obtained by trypsin digestion was GSSHHHHHHSSGLVPR (SEQ ID NO. 6), corresponding to 2-17 aa residues of the predicted Tgf2 transposase including the vector sequences and (His)6-tag. The molecular weight of the other two oligopeptide fragments were 1592.8 Da and 1650.9 Da respectively, and their sequences were identified as VFGVENNDIETEAR (SEQ ID NO. 7) and VLDQDDGFEFQLPK (SEQ ID NO. 8) respectively by tandem MS analysis (FIG. 5c, d). They respectively corresponded to aa residue sequences of 326-339 and 366-349 of the recombinant goldfish gfTP1 transposase, which were all located on the second exon. As shown in FIG. 5a, four cleavage sites of trypsin were observed before or after these fragments.

The results of western blotting assays and tandem MS analysis suggested that the recombinant protein of 79.4 kDa was successfully expressed in *E. coli* and confirmed to be recombinant goldfish gfTP1 transposase.

2.5. DNA Binding Activity Assay of Recombinant Goldfish gfTP1 Transposase

Whether the transposase can bind with transposon cis-element relates to transposition activity of the transposase. The binding ability of the purified recombinant goldfish gfTP1 transposase to the cis-element of Tgf2 transposon could be identified by EMSA. In this experiment, two DNA probes respectively corresponding to 5' and 3' end of Tgf2 transposon were synthesized, labeled by biotin, and then incubated with recombinant goldfish gfTP1 transposase at 25° C. for 0.5-1 h.

Figure 6:
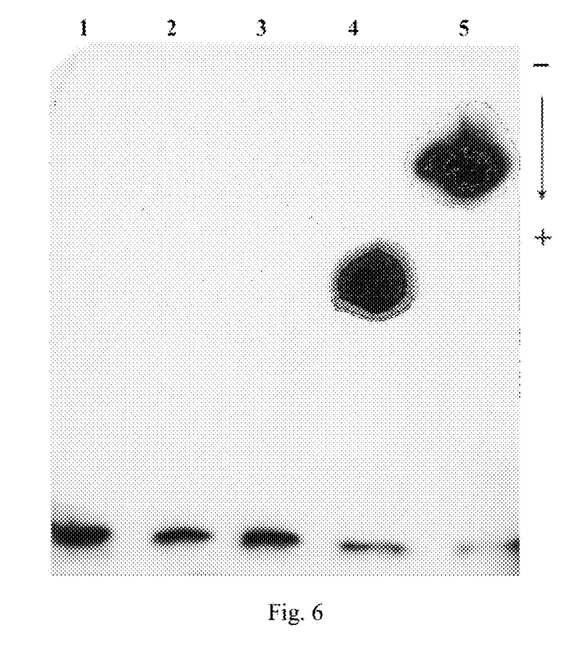

The results showed that electrophoretic mobility of the complex of 1× recombinant goldfish gfTP1 transposase and Tgf2 transposon probes was obviously slower than that of free probes, while no binding signal was detected in the group of the biotin-labeled probes for left (or right) arm (FIG. 6, lane 1), and the group of non-induced lysate (FIG. 6, lane 2). No binding signal was also detected in the complex group of biotin-labeled cold probes for control and the purified recombinant goldfish gfTP1 transposase (FIG. 6, lane 3). Additionally, the electrophoretic mobility of the complex of 10× recombinant goldfish gfTP1 transposase and the probes (FIG. 6, lane 5) was obviously slower than that of the complex of 1× recombinant goldfish gfTP1 transposase and the probes (FIG. 6, lane 4), because 10× recombinant goldfish gfTP1 transposase could form oligomer. These results indicated that the recombinant goldfish gfTP1 transpopsase had binding activity with DNA cis-element of goldfish Tgf2 transposon.

Embodiment 2 Optimization of Expression Conditions of the Recombinant Goldfish gfTP1 Transposase Protein According to the method of embodiment 1, The *Rosetta* 1 (DE3) *E. coli* cells carrying the recombinant plasmid pET28a-gfTP1 were cultured overnight, then 4 ml bacterial liquid was added to 100 ml of LB medium and shaken at 37° C. When the culture reached a predetermined $OD_{600}$ value, IPTG at certain concentrations was added to induce the expression of recombinant goldfish gfTP1 transposase protein, with additional shaking at 200 rpm at certain temperatures for 4 h. 5 experimental groups were set (Table 1) and repeated 5 times respectively.

TABLE 1

Experimental Groups

| Experimental group No. | $OD_{600}$ value of the culture when IPTG was added | Terminal concentration of IPTG (mM) | Culture temperature (° C.) |
|---|---|---|---|
| Experimental Group 1 | 0.3 | 0.6 | 21 |
| Experimental Group 2 | 0.4 | 0.7 | 22 |
| Experimental Group 3 | 0.3 | 1.0 | 22 |
| Experimental Group 4 | 0.6 | 0.7 | 24 |
| Experimental Group 5 | 0.5 | 0.8 | 23 |

According to the method of embodiment 1, the cells were collected, lysed and centrifuged after culture. The supernatant was collected and purified by $Ni^{2+}$-affinity column. Protein concentrations were monitored at 280 nm. The purities of supernatant and elution peak was analyzed by SDS-PAGE, and calculated by Gray-Scale after coomassie brilliant blue staining. The protein liquid was concentrated by ultrafiltration. The differences of protein expression levels among groups were analyzed by one-way ANOVA.

The results were shown in Table. 2, indicating that the total amounts of recombinant goldfish gfTP1 transposase protein in experimental group 1-3 were all significantly higher than that of experimental group 4 ($P<0.05$) or 5 ($P<0.05$).

TABLE 2

The Protein Expression Amount of Every Experimental Group

| Experimental group No. | Proportion of the recombinant goldfish gfTP1 transposase protein to total protein (%) | | Total amount of the recombinant goldfish gfTP1 transposase protein (µg) |
|---|---|---|---|
| | The supernatant after cell lysis | The elution peak | |
| Experimental Group 1 | 5.0 | 50 | 1200 |
| Experimental Group 2 | 4.1 | 38 | 800 |
| Experimental Group 3 | 3.2 | 33 | 600 |
| Experimental Group 4 | 0.7 | 5.1 | 76 |
| Experimental Group 5 | 0.8 | 5.1 | 83 |

Embodiment 3 Expression of Recombinant Goldfish gfTP1 Transposase Protein

According to the method of embodiment 1, the *Rosetta* 1 (DE3) *E. coli* cells carrying the recombinant plasmid pET28a-gfTP1 were cultured overnight, then 4 ml bacterial liquid was added to 100 ml of LB medium and shaken at 36° C. When $OD_{600}$ value of the culture reached 0.35, IPTG was added to 0.8 mM terminal concentration to induce protein expression, with additional shaking at 150 rpm at 21° C. for 6 h.

Proportion of the recombinant goldfish gfTP1 transposase protein to total protein was calculated according to the method of embodiment 2, with the results that proportion of the recombinant goldfish gfTP1 transposase protein to total protein in the supernatant after cell lysis was 3.6%, and proportion of the recombinant goldfish gfTP1 transposase protein to total protein in the elution peak was 35%. The total amount of the recombinant goldfish gfTP1 transposase protein was 642 µg.

Embodiment 4 Transgenic Effect of Recombinant Goldfish gfTP1 Transposase Protein in Zebrafish (*Danio rerio*)

Zebrafish feeding: the male and female zebrafish for experiment were reared respectively in cycle aquarium at a constant temperature of 28° C. in the condition that 14 h light and 10 h darkness were alternately provided, and fed 2 times per day, one time was given artemia, the other time artificial feed. Males and females zebrafish were put into the same small aquarium with a transparent baffle for dividing the two sex zebrafish at the night before spawning. The baffle was taken away to let the female zebrafish lay eggs and eggs were fertilized naturally in the morning of experiment day.

Figure 7:
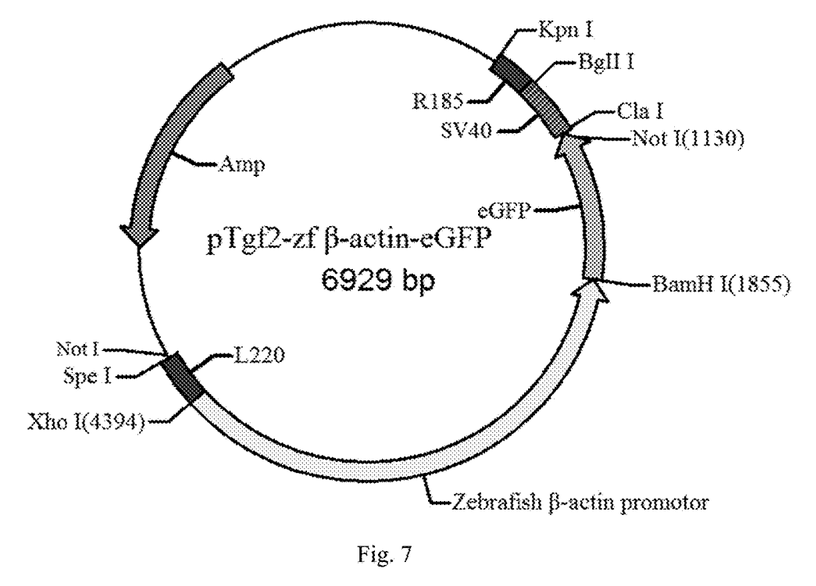
FIG. 7 shows the vector map of donor plasmid pTgf2-zfβ-actin-eGFP for transgene.

Microinjection: A mixture solution of the transgenic donor plasmid pTgf2-zfβ-actin-eGFP with the terminal concentration of 50 ng/μl prepared using 0.3× Danieau buffer (containing 0.1% phenol red) and the purified 1× recombinant goldfish gfTP1 transposase protein (720 aa) expressed as embodiment 1 said were used for microinjection. The vector map of the plasmid pTgf2-zfβ-actin-eGFP was shown in FIG. 7, and you can additionally refer to Chinese Patent No. ZL2010102231888 with the title "a transgenic method in fish based on Tgf2 transposon, the vector and construction method of the vector". The microinjection apparatus PV830 Pneumatic Pico Pump (US, WPI) driven by $N_2$ was used to carry out microinjection. The microinjection needle was drawn from glass capillaries of 1 mm diameter by microinjection needle-elongated device and the tip of the needle was removed by tweezers when used. The mixture solution of the transgenic donor plasmid and recombinant goldfish gfTP1 transposase protein was added into the microinjection needle, and injected into the yolk of zebrafish embryos at the 1-2 cell stage near to cells. $1\times10^{-3}$ μl solution containing ~50 pg transgenic donor plasmid and 1× recombinant goldfish gfTP1 transposase protein was injected to each embryo. After injection, the embryos were placed in embryo rearing medium at 28° C. to develop normally and the fluorescent expression in embryos was analyzed regularly (every 6 hours) using a fluorescence microscope.

Figure 8:
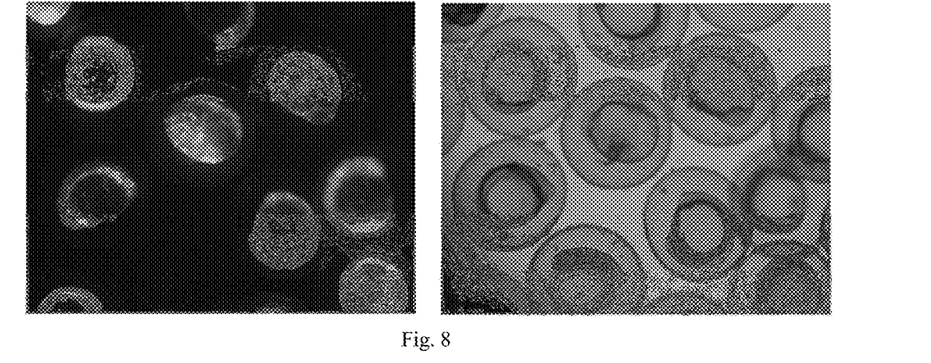
FIG. 8 are images of EGFP expression in zebrafish fertilized eggs at 12 h after co-injection of the donor plasmid pTgf2-zfβ-actin-eGFP and recombinant goldfish gfTP1 transpopsase. The left is fluorescence image, showing strong and almost ubiquitous expression of EGFP. The right is the normal white light image.

Result 1: Fluorescence microscopy images of EGFP expression in zebrafish fertilized eggs at 12 h after co-injection of the donor plasmid pTgf2-zfβ-actin-eGFP and the recombinant goldfish gfTP1 transpopsase were shown in FIG. 8, indicating that EGFP was expressed strongly and ubiquitously. There were 245 surviving embryos and 201 embryos expressing EGFP strongly and ubiquitously at 36 h after co-injection of the donor plasmid pTgf2-zfβ-actin-eGFP and the recombinant goldfish gfTP1 transpopsase, demonstrating the rate of positive EGFP expression was 82.0%. Among 201 EGFP expressing embryos, there were 112 zebrafish larvae expressing EGFP after 6 days, demonstrating the integration rate of EGFP was 55.7%. Result 2: In another experimental group, there were 158 surviving embryos and 87 embryos expressing EGFP strongly and ubiquitously at 36 h after co-injection, demonstrating the rate of positive EGFP expression was 55.1%, while there were 44 zebrafish larvae expressing EGFP after 6 days, demonstrating the integration rate of EGFP was 50.6%.

Embodiment 5 Transgenic Effect of Recombinant Goldfish gfTP1 Transposase Protein in Blunt Snout Bream (*Megalobrama amblycephala*)

The experiments of induced spawning, artificial insemination, incubation and culture of the blunt snout bream were carried out at the Genetics and Breeding Center for Blunt Snout Bream of Agriculture Ministry of Shanghai Ocean University. The parents of blunt snout bream were all 3 years old, having sexual maturity and good development. The artificial induced spawning for female fish was carried out at 4 p.m by injection with spawning induced drugs of LHRH-A2 (5 μ/Kg) and HCG (1000 U/Kg), and the half of the dosage injection for male fish. The parent fish injected with spawning induced drugs were temporarily put in circular spawning pool (2 m diameter) under flowing water stimulation, and netted to take sperms and eggs to conduct artificial dry insemination in the next morning.

Microinjection: A mixture solution of the transgenic donor plasmid pTgf2-zfβ-actin-eGFP with the terminal concentration of 50 ng/μl prepared using 0.3× Danieau buffer (containing 0.1% phenol red) and the purified 1× recombinant goldfish gfTP1 transposase protein (720 aa) expressed as embodiment 1 said were used for microinjection. The microinjection apparatus PV830 Pneumatic Pico Pump (US, WPI) driven by $N_2$ was used to carry out microinjection. The microinjection needle was drawn from glass capillaries of 1 mm diameter by microinjection needle-elongated device and the tip of the needle was removed by tweezers when used. The mixture solution of the transgenic donor plasmid and recombinant goldfish gfTP1 transposase protein was added into the microinjection needle, and injected into the yolk of blunt snout bream embryos at the 1-2 cell stage near to cells. $1\times10^{-3}$ μl solution containing ~50 pg transgenic donor plasmid and 2 ng recombinant goldfish gfTP1 transposase protein was injected into each embryo. After injection, embryos were placed in incubator to incubate with water alteration every 3-4 hours until hatching, and the fluorescent expression in embryos was analyzed regularly (every 6 hours) using fluorescence microscope.

Figure 9:
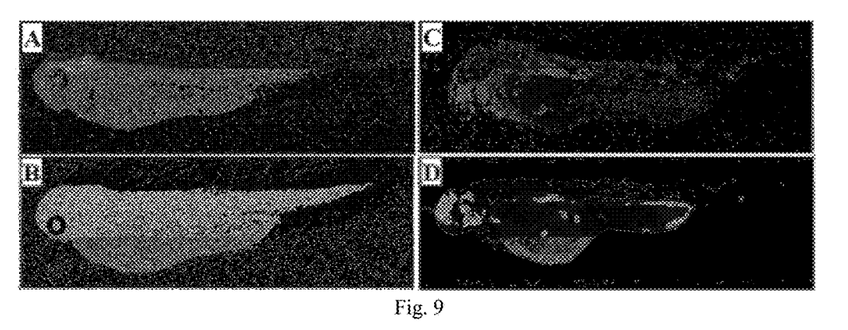
Figure 10:
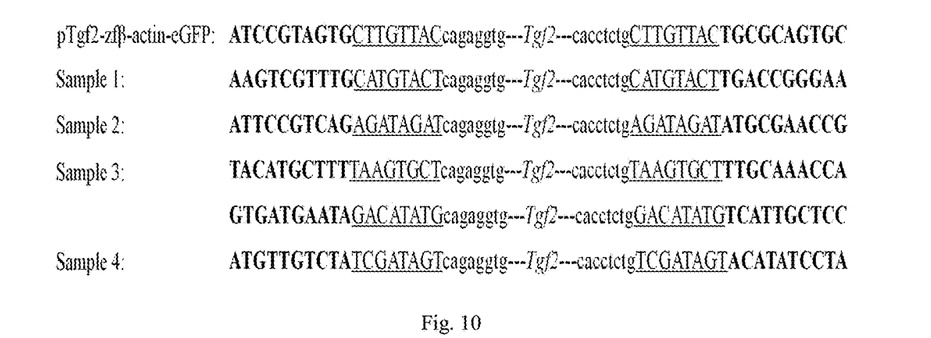
FIG. 10 shows the flanking sequences of insertion site in genome of one-year-old blunt snout bream co-injected the donor plasmid pTgf2-zfβ-actin-eGFP and recombinant goldfish gfTP1 transpopsase. The surrounding sequences of insertion site in blunt snout bream genome is in uppercase and boldface. The end sequence of Tgf2 transposon is in lowercase. The 8-bp direct repeat sequences are marked by underline.

Fluorescence microscopy images of EGFP expression in blunt snout bream fertilized eggs at 72 h after co-injection of the donor plasmid pTgf2-zfβ-actin-eGFP and recombinant goldfish gfTP1 transpopsase were shown in FIG. 9*a, b*, showing that EGFP was expressed strongly and ubiquitously in 74% (393/525) of the embryos, while a weak EGFP expression in part of the cells was detected in 31% (27/86) of the control embryos only injected the donor plasmid pTgf2-zfβ-actin-eGFP (FIG. 9*c,d*). The injected blunt snout bream were transferred into 20 m×30 m earth pond to be fed. The integration rate of EGFP in one-year-old blunt snout bream co-injected the donor plasmid pTgf2-zfβ-actin-eGFP and recombinant goldfish gfTP1 transpopsase, as determined by PCR using DNA from tail fins, reached 45% (35/77). In comparison, the integration rate of EGFP in blunt snout bream only injected the donor plasmid pTgf2-zfβ-actin-eGFP for control was only 10% (2/20). The insertions of Tgf2 transposon in blunt snout bream genome were further detected by inverse PCR (Reference: Chinese Patent No. CN102628083B with the title "a method to determine flanking sequence and copy number of Tgf2 transposon in goldfish genome"). There were 1-2 insertion sites of transposon in transgene-positive adult fish of blunt snout bream co-injected the donor plasmid pTgf2-zfβ-actin-eGFP and recombinant goldfish gfTP1 transpopsase. An 8-bp direct repeat, the signature of hAT family transposons, was created adjacent to both ends of the insertion sites (FIG. 10), indicating the recombinant goldfish gfTP1 transposase protein could mediate efficient and precise integration of the donor plasmid pTgf2-zfβ-actin-eGFP in blunt snout bream genome.

The present invention is not intended to limit to embodiments thereof. Further, it will be understood by those skilled in the art that various changes in form and details may be made therein without departing from the spirit and scope of the invention as defined by the appended claims.

The invention claimed is:

1. A method of expressing goldfish gfTP1 transposase protein comprising:
   a) culturing *E. coli* Rosetta 1 (DE3) transformed with a pET-28A plasmid comprising a nucleic acid encoding the goldfish gfTP1 transposase protein encoded by SEQ ID NO: 5, wherein the nucleic acid is inserted between BamHI and XhoI sites, until the optical density at a wavelength of 600 nm (OD600) value of the culture reaches 0.3-0.4;
   b) adding isopropyl beta-D-thiogalactoside (IPTG);
   c) shaking the culturing from b) at 150-200 rpm at 21-22° C., thereby expressing the goldfish gfTP1 transposase protein.

2. The method of claim 1, wherein the *E. coli* Rosetta 1 (DE3) is cultured until the OD600 value of the culture reaches 0.35 in step a), the ITPG is added in step b) and the resultant culture in step b) is shaken at 150-200 rpm at 22° C.

3. The method of claim 1, wherein the time of shaking is 4-6 h.

4. The method of claim 1, wherein the concentration of IPTG in culture is 0.6-1.0 mM.

5. A pET-28A plasmid comprising a nucleic acid encoding the goldfish gfTP1 transposase protein encoded by SEQ ID NO: 5, wherein the nucleic acid is inserted between BamHI and XhoI sites.

6. A culture comprising *E. coli* Rosetta 1 (DE3) transformed with the plasmid of claim 5.

* * * * *